United States Patent [19]

Cottenceau et al.

[11] Patent Number: 5,375,612
[45] Date of Patent: Dec. 27, 1994

[54] POSSIBLY ABSORBABLE BLOOD FILTER

[75] Inventors: Jean-Philippe Cottenceau, Antony; Gérard Chevillon, Montrouge; Maurice Roussigne; Guy Nadal, both of Poitiers, all of France

[73] Assignee: B. Braun Celsa, Chasseneuil, France

[21] Appl. No.: 40,259

[22] Filed: Mar. 30, 1993

[30] Foreign Application Priority Data

Apr. 7, 1992 [FR] France ................. 92 04226

[51] Int. Cl.5 ............... A61M 29/00; A61B 19/00
[52] U.S. Cl. .................. 128/899; 606/194; 606/200
[58] Field of Search ............... 128/897–899; 606/191, 194, 198, 200

[56] References Cited

U.S. PATENT DOCUMENTS

| | | | |
|---|---|---|---|
| 4,727,873 | 3/1988 | Mobin-Uddin | 606/200 |
| 4,817,600 | 4/1989 | Herms et al. | 606/198 |
| 4,873,978 | 10/1989 | Ginsburg | 606/200 |
| 4,990,156 | 2/1991 | Lefebvre | 606/200 |
| 5,035,706 | 7/1991 | Giantureo et al. | 606/198 |
| 5,108,418 | 4/1992 | Lefebvre | 606/200 |

FOREIGN PATENT DOCUMENTS

| | | | |
|---|---|---|---|
| 0420541 | 4/1991 | European Pat. Off. | |
| 0423916 | 4/1991 | European Pat. Off. | |
| 2567405 | 1/1986 | France . | |
| 2573646 | 5/1986 | France | 128/898 |
| 2580504 | 10/1986 | France . | |
| 3900517 | 7/1989 | Germany | 606/200 |

*Primary Examiner*—Lee S. Cohen
*Assistant Examiner*—J. P. Lacyk
*Attorney, Agent, or Firm*—Pollock, Vande Sande & Priddy

[57] ABSTRACT

The invention relates to an implantable blood filter comprising a self-expanding external structure made from a zigzagged thread wound on itself in order to exhibit a closed configuration. A central strainer section is connected to the said thread at various points for the retention of possible blood clots. This strainer section may be made from a biologically absorbable material. Applications include the production of medical blood filters, which are self-centering and absorbable.

19 Claims, 3 Drawing Sheets

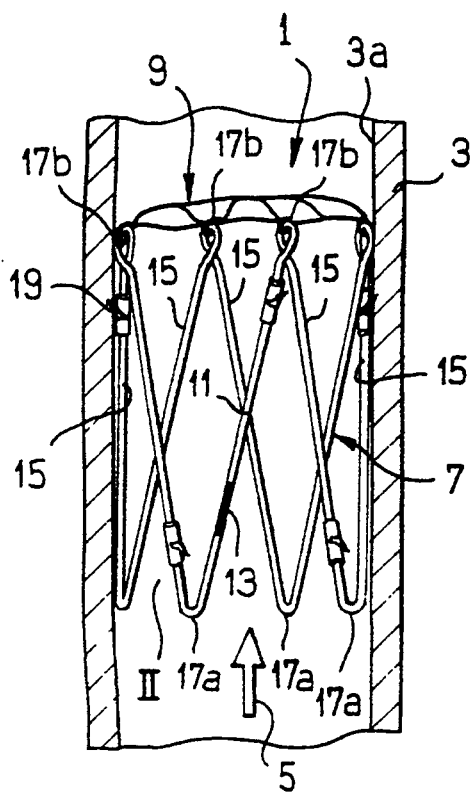
FIG_1
FIG_2
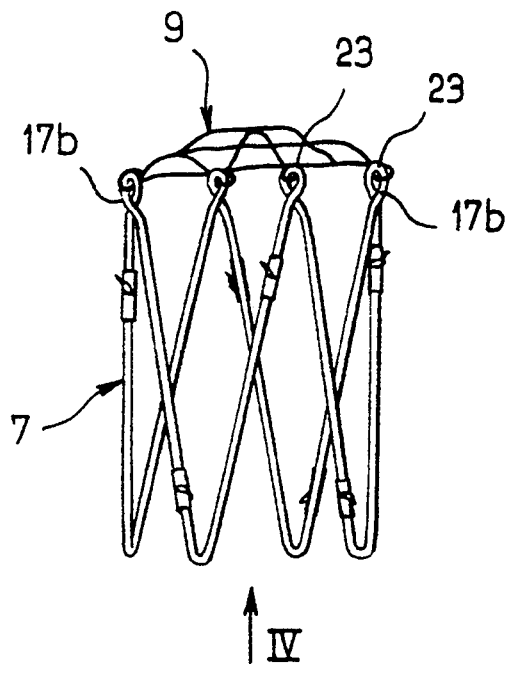
FIG_3
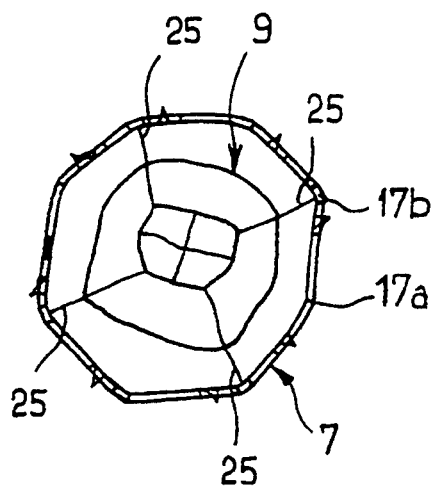
FIG_4

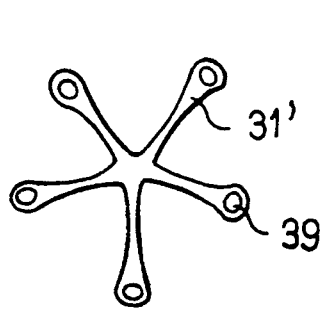
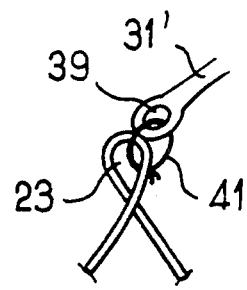
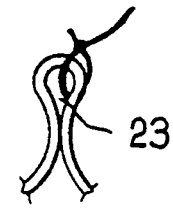
FIG_10   FIG_11   FIG_12
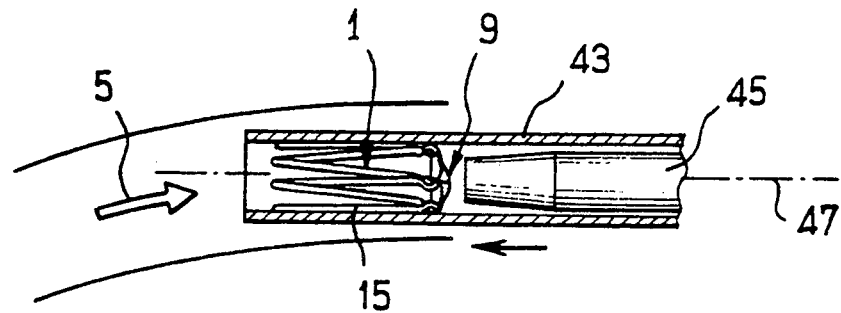
FIG_13
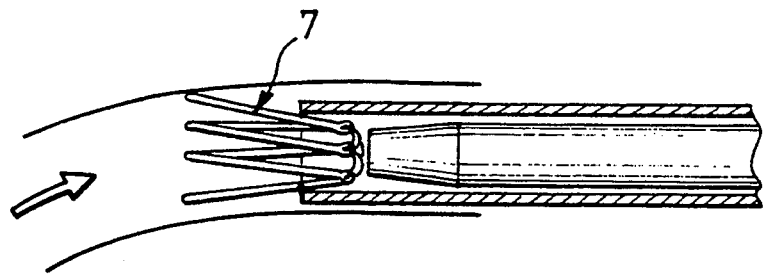
FIG_14
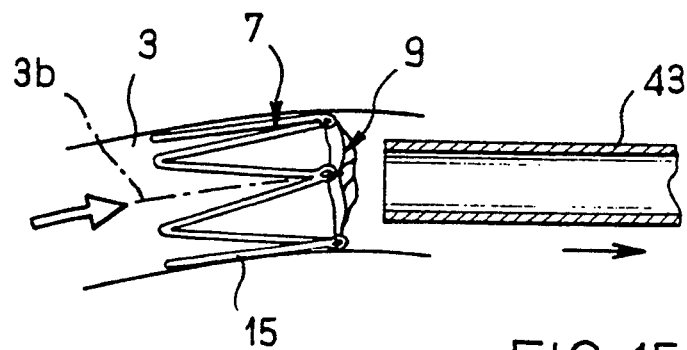
FIG_15

5,375,612

POSSIBLY ABSORBABLE BLOOD FILTER

FIELD OF THE INVENTION

The subject of the invention is an improved blood filter intended to be placed or implanted in a vessel of the circulatory system, in order to retain therein possible blood clots.

Filters of this type are, for example, described in U.S. Pat. No. 3,952,747, EP-A-293,605 or again EP-A-188,927.

BACKGROUND OF THE INVENTION

In general, these filters are in the shape of a small frustoconical basket which is attached to the inside of the vessel in which it is implanted, downstream of the course which it is desired to filter; this is in general the vena cava arriving at the heart.

It is thus possible to stop, before they enter the heart, possible blood clots which can form and risk causing in particular embolisms.

One difficulty characteristic to this type of operation consists in positioning the filter correctly. In general, in order to introduce such a filter into the vessel, it is pushed therein by means of a tube which passes through the said vessel and whose diameter is less than that of the latter. When the filter reaches the end of the introduction tube, it is then released into the vessel and the expansion of its feet, which are often fitted with hooks, anchors it.

Such a "release" is in practice very tricky to control, and it has been shown in numerous cases that the basket filter in fact occupied, inside the vessel, a position other than the most favourable position with its axis substantially parallel to the axis of the vessel.

The invention which is the subject of Patent EP-A-188,927 provided a first solution to this centering problem, by providing for the feet of the filter to be provided, towards their free end, with appendages oriented substantially parallel to the cylindrical wall generated by a generator line parallel to the axis of the conical corolla of the filter.

Obviously, since the invention of this filter, research has continued.

During this research, it has in particular been shown that it could be advantageous to be able, in certain cases and if necessary, to make at least the actually filtering part of the filter (that is to say its part extending as far as the centre of the vessel) absorbable, while possibly keeping the most external part for attachment to the vessel unabsorbable, while still ensuring the best possible centering of the filter.

Known filters in the shape of a frustoconical basket have been shown to exhibit certain drawbacks linked in particular with the fact that if it was desired to make the central filtering part absorbable, the peripheral parts used for attachment risked becoming, after absorption of this central part, mutually disconnected, with, as a consequence, significant risks of detachment, with the obvious problems.

BRIEF DESCRIPTION OF THE INVENTION

The object of the invention is to solve these difficulties by providing an improved self-centering blood filter which is designed in order possibly to be at least partly biologically absorbable, and comprising for this purpose:

a self-expanding external structure comprising at least one relatively rigid thread shaped in a zigzag and wound in order to exhibit a closed configuration, and a central sieving part connected to the said thread at various points, for the retention of possible blood clots.

Advantageously, the zigzagged thread will have a set of lines connected by curved end portions and will be able elastically to occupy a first stressed folded position in which the said lines will extend substantially side by side along each other, in order to allow the introduction of the filter into the circulatory system, and a second unfolded position in which the said lines will separate angularly from each other in order to define a substantially cylindrical tubular surface matching the receiving vessel.

According to another characteristic of the invention, the external structure for holding the filter will extend exclusively at the periphery of the latter, the connection between this structure and the central sieving part being situated at the periphery of this said part.

Thus, if, as an additional characteristic of the invention provides, the central sieving part is made from a biologically absorbable material, the risks of migration of the external structure (here assumed to be unabsorbable) will be very limited, taking into account the shape of this structure, and this will be all the more true since its zigzagged lines should come substantially into contact with the vessel when the filter is implanted.

As regards the structure of the central filtering or sieving part, the latter may in particular be made from a filament or a series of relatively flexible filaments arranged for example in order to constitute a meshed net or alternatively such that these filaments join or interweave in the manner of a bundle in a substantially central zone of the filter.

In particular, if this sieving part is to be absorbable, filaments of different cross sections may be used in order to reduce the resistance to absorption towards the centre of the vessel.

The central part in question may, however, also have the shape of a monobloc star with several branches joined together towards the centre of the star, and possibly even with additional ramifications for the intermediate connection of the branches.

A more detailed description of the invention will now be given, referring for this purpose to the accompanying drawings which are given solely by way of non-limiting examples, and in which:

BRIEF DESCRIPTION OF THE FIGURES

FIG. 1 is a diagrammatic view of a filter according to the invention implanted in a vessel, FIG. 2 is a detailed view of the hook corresponding to the reference II in FIG. 1, FIG. 3 is a view of the filter in FIG. 1 alone in its expanded state but not implanted, FIG. 4 is a bottom view of the filter in FIG. 3 in the direction of the arrow IV, FIG. 10 is another variant embodiment of a sieving part which can be used on a filter of the invention, FIGS. 11 and 12 show two possible variant embodiments of the end eyes of the zigzagged structure and their connection with the sieving part, and FIGS. 13 to 15 diagrammatically show, in three successive characteristic steps, a possible fitting of a type of blood filter according to the invention.

DETAILED DESCRIPTION OF THE INVENTION

Figure 5:
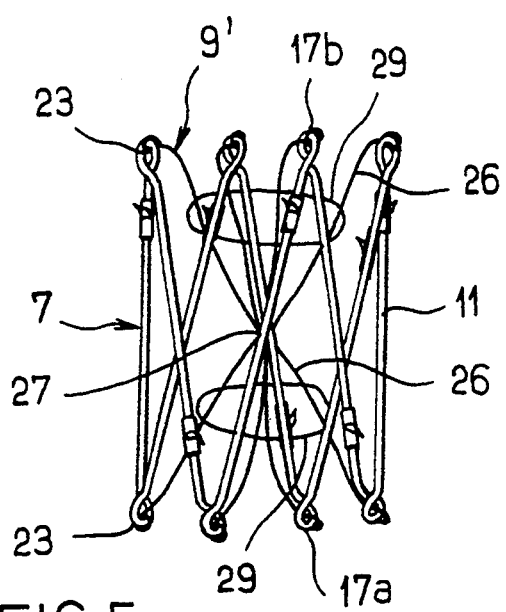
FIG. 5 is a variant embodiment of the filter.

Referring first of all to FIG. 1, an illustration is thus seen of a filter 1 here implanted in the unfolded position inside a vessel 3 so as to be able to intercept possible blood clots which can flow therein, the direction of the blood flow having been shown by the arrow 5.

According to the invention, the filter 1 comprises a central filtering part 9 intended for the retention of possible blood clots and peripherally connected to the external structure 7 which is self-expanding (or extensible) 4 in order, once the filter has been released, to hold the latter centered substantially at its location of implantation.

As can be seen, the holding structure 7 consists for this purpose of at least one relatively rigid thread 11, shaped in a zigzag and wound on itself in order to exhibit a closed configuration defining, in the case in point, a substantially cylindrical tubular surface applied against the internal wall 3a of the vessel 3 which may, for example, be the vena cava.

The zone of closure of the zigzagged thread where its two ends join has been represented as 13, and the references 15 and 17a, 17b respectively designate the sets of lines and the curved end portions of the thread.

Thus configured, this holding structure therefore extends only in immediate proximity to the wall of the vessel, almost without interfering with the space reserved for the flow of blood, the lines 15 of the structure having a priori to come substantially into contact with the wall 3a.

Such an arrangement naturally limits the risks of migration of the filter.

However, it is recommended further to provide attachment means, such as those referenced 19, which are to penetrate slightly into the wall of the vessel. These attachment means may in particular each consist of a hook projecting from a plate 21 welded to one of the lines 15, as is illustrated in FIG. 2. The added hooks in question may in particular extend in pairs in opposing directions, alternatively from one line to the other, so as to prevent any translation of the filter in one direction or in the opposite direction.

In the art, such a zigzagged structure (possibly provided with such additional attachment means) has in fact already been used for making vessel wideners commonly called "stents" and employed as a means for treating stenosis (illness linked with the narrowing of the blood vessels, creating severe circulation problems such as in particular atherosclerosis, phlebitis, etc.).

One method of treating these stenoses consists in installing inside the veins or arteries a balloon which is inflated in order locally to open out the narrowed vessel, after which a stent is installed at this location, the stent then acting as a widener or reinforcing support for preventing the vessel from again narrowing at the location where the device is placed, another function being to hold applied onto itself a part of the wall of the vessel which was capable of detaching therefrom, or furthermore to prevent the future blockage of the vessel following the progression of the atheromatous illness.

None of these functions is provided by the blood filter of the invention, nor in particular by its holding structure 7 whose role is to act as a means for holding the filter in position, once implanted, and for supporting the attachment means 19, concomitantly holding the central sieving or filtering part 9.

In other words, like any blood filter, that of the invention cannot in any case be confused with a "stent", their fields of application being moreover different: blood disorder for the filter (possible migration of clots) and distortion of a vessel wall (stenosis) for the stent.

To return more specifically to the filter of the invention, reference will now be made more particularly to FIGS. 2 and 3, in which the filter of FIG. 1 is here found represented not implanted but still in its expanded or unfolded state.

In addition to what has already been stated, it will be noticed on these figures that the curved end portions 17b of the zigzagged structure 7 each here have an eye 23 for the peripheral fastening of the central sieving part 9.

In the case in point, this part 9 is in the form of a net or a "spider's web" made from one or more deformable filaments, connected together in order to constitute a meshed net, which is peripherally connected to the structure 7 at the location of the eyes 23, for example by knots (see FIG. 4).

In particular, such a net may be made from a filament normally employed for surgical sutures.

While it is considered a priori inappropriate to use an absorbable material for the "rigid" thread which is to constitute the zigzagged structure 7 (a structure made of "phynox"—registered trademark—or alternatively from stainless steel, or from titanium, then being recommended, it is conversely quite envisageable to use absorbable suture filaments in order to produce the net 9.

It is then possible for example to employ woven monofilaments of poly(glycolic acid) or alternatively of a copolymer of glycolic acid.

By way of variant, Patent FR-A-2,635,966 describes the possible use of fibres based on poly-p-dioxanone and on a polygalactan.

If in contrast unabsorbable suture threads are preferred, materials may be employed ranging from a metal filament to synthetic materials (polyester, polyamide), or alternatively natural silk and flax threads.

If, however, the solution of an absorbable sieving part 9 is adopted, it is then recommended to provide a resistance to biological absorption of this sieving part, once the filter is implanted, which is less towards a substantially central zone of the latter than at its periphery where the said sieving part is connected to the structure 7.

Thus, the filter will lose its filtering power only progressively, this period extending over several months, or even several years.

This effect may in particular by obtained by making the net 9 with smaller mesh openings towards the centre than towards the periphery and/or providing filaments with different cross sections which may narrow as the centre of the net is approached.

By way of example, such threads could have diameters between 0.7 to 5 tenths of millimeters.

Another embodiment of the filter of the invention has been illustrated in FIG. 5.

Figure 6:
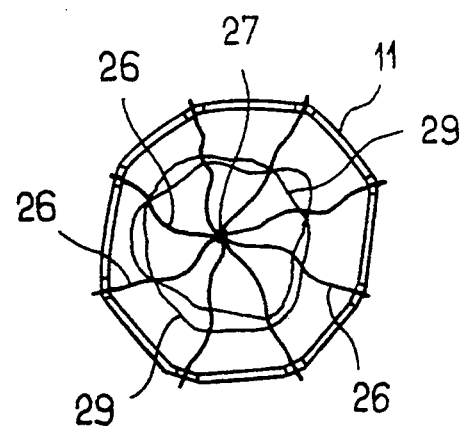
FIG. 6 is a bottom view of the filter in FIG. 5, in the direction of the arrow VI.

In fact, this variant differs from the previous one essentially only on two points: on the one hand, the structure 7 now has eyes 23 at both of its opposite ends 17a, 17b, and the central filtering part, here referenced 9', now consists of a series of filaments (absorbable or not, as before) connected to the said structure 7 (for example knotted) at the location of the eyes 23, this being at one or other of the said ends 17a, 17b, the filaments being arranged so as to join or interweave, in the manner of a network or a bundle 26, in a substantially central zone of the filter, as is clearly seen when comparing FIGS. 5 and 6 in which the central interweaving part has moreover been referenced 27.

Thus, the central sieving part 9' will in some way have a double inverted truncated cone configuration occupying the central volume of the filter externally delimited by the zigzagged thread 11.

As before, the filaments of the sieve 9' may be absorbable by biological means and have different diameters.

Possibly, the bundle of threads 26 may be supplemented by one or two hoopings of threads such as 29 of reduced cross section, locally surrounding at two intermediate levels the said "main" threads 26, so as thus to increase the filtering power of the filter at least temporarily.

Figure 7:
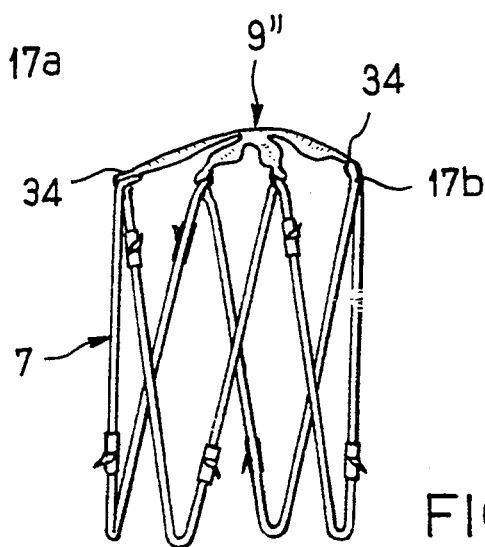
FIG. 7 is another variant embodiment of the filter.
Figure 8:
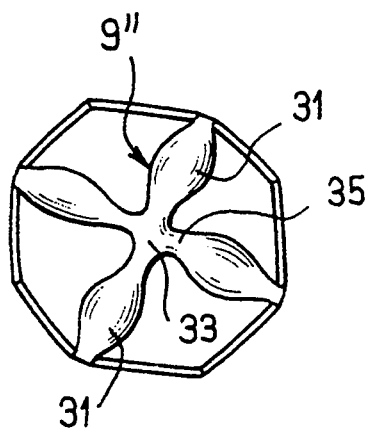
FIG. 8 is a bottom view of the same filter, in the direction of the arrow VIII in FIG. 7.

FIGS. 7 and 8 illustrate another variant in which the zigzagged structure 7 is now deprived of end eyes, the central sieving part, here referenced 9", is in the form of a flexible monobloc star (see FIG. 8) with several branches 31 connected together towards the centre of the star, at 33, and capable, for example, of being adhesively bonded peripherally to the end edges 34, at the location of the curved connection portions 17b of the filter.

In particular, in the case in which this "filtering star" is made from an absorbable material, the branches will locally exhibit, in proximity to the centre 33, a reduced cross section such as that referenced 35 in FIG. 8 for one of the branches.

In practice, the star in question may in particular be made by moulding, cutting or punching for example from a sheet or a thin plate of an appropriate material. Obviously, the branches may be very thin.

If the star is to be biologically absorbable, poly(glycolic acid) or a poly(lactic acid) may then in particular be used.

Also, in order locally to reduce the cross section of this star, as at 35, this effect may be obtained either by reducing its width or by reducing its thickness. A plate having a concave surface on one side may then be used.

Figure 9:
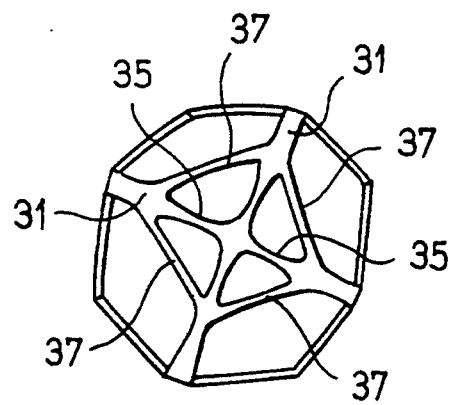
FIG. 9 is a variant embodiment of the sieving part of the filter in FIG. 8.

Possibly, the branches 31 might furthermore be connected in pairs by intermediate transverse ramifications such as those referenced 37 in FIG. 9, extending between the centre and the periphery of the star.

Obviously, star shapes other than those in FIGS. 8 and 9 could be adopted.

Thus, the shape in FIG. 10 is envisagable. Although the branches of the star in FIG. 8 first bulge outwards towards the periphery before becoming constricted at 35, the branches 31' of the star in FIG. 10 narrow directly from the periphery. In contrast, there are more of them. Furthermore, these branches are pierced at 39 at their widened free end so as to exhibit there an orifice which can be passed through by a tie (such as an unabsorbable suture filament) which can be knotted into each of the eyes 23 which the structure 7 would then exhibit at the corresponding end, as is illustrated in FIG. 11.

In FIG. 12, a detail view has been illustrated showing at the same location the fastening of a filament which can be used for the filter in FIGS. 3 and 5.

In FIGS. 11 and 12, two possible embodiments of the eyes 23 will also be observed: with crossover (FIG. 11), or with simple squashing or local constriction, without crossover or overlap (FIG. 12).

In FIGS. 13 et seq., a possible mode of introduction of the filter of the invention has been illustrated diagrammatically.

Fitting of the filter is done percutaneously (normally via the jugular or femu), through an introduction tube referenced 43 and normally called in the art "Desilet".

The filter 1 is pushed into the tube 43 by the pusher 45.

It will be observed that when in place in the tube, the filter then elastically occupies its stressed folded position, in which the lines 15 of its zigzagged thread extend substantially side by side along each other, more or less parallel to the axis 47 of the tube.

It will furthermore be noted that the filter has been placed so that its sieving part 9 leaves last, the tube 43 having been introduced against the direction of the blood flow (arrow 5).

In FIG. 14, the filter is shown with its structure 7 already leaving the tube and being substantially corolla-shaped.

In FIG. 15, the filter is seen an instant later, fully unfolded, with its structure 7 completely freed. The zigzagged thread is then elastically unfolded, defining a substantially cylindrical envelope which is almost coaxial with the axis 3b of the vessel, the elastic separation of the lines of the thread leading to attachment of the filter and coroṇa-type unfolding of the central filtering part 9 which is then perfectly able to perform its filtering role.

The tube 43 may then be retracted through its access site.

It is obvious that the variant embodiments of the filter in FIGS. 5 to 10 may be introduced in the same manner.

As regards the embodiment of the structure 7, it will merely be noted that it may easily be obtained from a thread made of an adapted material, shaped flat into a zigzag, then closed on itself in order to join its two ends so as then to define a sort of substantially cylindrical shell in its state expanded transversely or radially to its cylindrical axis, and obtained for example from a round steel thread with a diameter of a few tenths of millimeters, in particular 4 to 8 tenths.

We claim:

1. A blood filter comprising:
   a wire formed in a zigzag configuration including
   an endless series of straight sections being joined by bends at opposite ends to form, upon expansion in a blood vessel, a cylindrical, open tubular wall;
   and separate filtering means connected to the tubular wall, and extending therein, to cover at least one end of the tubular wall for filtering encountered blood clots.

2. The filter set forth in claim 1 wherein the wire is flexible and therefore allows contraction of the zigzag configuration during installation of the filter into the vessel.

3. The filter set forth in claim 1 further comprising:
   retaining means attached to the wire and adapted to penetrate the blood vessel for anchoring the filter within the vessel.

4. A blood filter comprising:

a flexible wire formed in a zigzag configuration including an endless series of straight sections being joined by bends at opposite ends to form, upon expansion in a blood vessel, a cylindrical, open tubular wall:

separate filtering means connected to the tubular wall, and extending therein, to cover at least one end of the tubular wall for filtering encountered blood clots; and retaining means extending from the wire and adapted to penetrate the blood vessel for anchoring the filter within the vessel.

5. The filter set forth in claim 1 or 4 wherein the cross-section of the tubular wall increases upon its expansion, after installation in the blood vessel.

6. The filter set forth in claim 1 or 4 wherein the separate filtering means is attached along its periphery to the tubular wall.

7. The filter set forth in claim 1 or 4 wherein:

the filtering means further comprises a material which is biologically absorbed when the filter has been implanted for a predetermined time; and further wherein a central portion of the filter means is more quickly absorbed than the periphery thereof.

8. The filter set forth in claim 4 wherein the zigzag configuration comprises multiple pairs of straight line sections connected by an intermediate bend.

9. The filter set forth in claim 1 or 4 wherein the filtering means further comprises a flexible filament material forming a strainer with smaller mesh openings in a central portion than at the periphery thereof.

10. The filter set forth in claim 1 or 4 wherein the filtering means further comprises a flexible filament material which is thinner at a central portion than at the periphery thereof.

11. The filter set forth in claim 1 or 4 wherein the filtering means further comprises:

a flexible filament material extending inside the zigzag wire configuration to form an hourglass shaped strainer peripherally attached to opposite ends of the configuration and having a longitudinally disposed junction point located in a median axial zone of the configuration.

12. The filter set forth in claim 11 further comprising:

at least one transverse hoop of flexible filament located along the length of the hourglass shaped strainer for increasing filtering action.

13. The filter set forth in claim 1 or 4 wherein the filtering means further comprises a star shaped body having a plurality of arms radiating from a central point.

14. The filter set forth in claim 13 wherein the central point has a reduced thickness relative to the arms.

15. The filter set forth in claim 13 wherein the body further comprises branch sections interconnecting medial points along adjacent arms.

16. The filter set forth in claim 13 wherein the star shaped body is made from a material which is biologically absorbed after the filter is implanted for a preselected period of time, the material belonging to the group consisting of poly(glycolic acid) and poly(lactic acid).

17. The filter set forth in claim 9 wherein the filaments of the filtering means are fabricated from an absorbable suture material.

18. The filter set forth in claim 1 or 4 wherein the zigzags of the filter configuration have loop eyes formed at least one end of the tubular wall for connecting the filtering means thereto.

19. A blood filter device comprising:

an axially disposed tubular wall having openings therein;

first and second transverse ends defining axial limits of the wall:

the tubular wall formed from at least one wire having a zigzag configuration;

separate filtering means connected to the wall and extending therein to cover at least one of the transverse ends for trapping blood clots;

the filter device being sufficiently flexible to allow size reducing radial contraction thereof, relative to a central axis, to facilitate insertion of the filter into a blood vessel;

the filter device further being sufficiently resilient to cause radial expansion thereof within the blood vessel, the expansion limited by restraining contact of the tubular wall by a vessel.

* * * * *